United States Patent [19]

MacGregor Donaldson

[11] Patent Number: 5,838,420
[45] Date of Patent: *Nov. 17, 1998

[54] METHOD AND APPARATUS FOR OCULAR MOTILITY TESTING

[75] Inventor: William Blair MacGregor Donaldson, Aberdeen, United Kingdom

[73] Assignee: BID Instruments Limited, Aberdeen, United Kingdom

[ * ] Notice: The term of this patent shall not extend beyond the expiration date of Pat. No. 5,550,601.

[21] Appl. No.: 651,843

[22] Filed: May 21, 1996

Related U.S. Application Data

[63] Continuation-in-part of Ser. No. 313,051, Sep. 30, 1994, Pat. No. 5,550,601.

[51] Int. Cl.$^6$ ........................................................ A61B 3/14
[52] U.S. Cl. .......................... 351/209; 351/205; 351/246
[58] Field of Search ................................... 351/209, 205, 351/210, 211, 206, 246, 245, 221

[56] References Cited

U.S. PATENT DOCUMENTS

| | | | |
|---|---|---|---|
| 5,070,883 | 12/1991 | Kasahara | 128/745 |
| 5,094,521 | 3/1992 | Jolson et al. | 351/210 |
| 5,550,601 | 8/1996 | Donaldson | 351/209 |

*Primary Examiner*—Hung X. Dang
*Attorney, Agent, or Firm*—Woodcock Washburn Kurtz Mackiewicz & Norris, LLP

[57] ABSTRACT

Apparatus for ocular motility testing comprising, an item of headgear 5 onto which is mounted: gaze-detection means 25 for determining the visual axis directions of one or both eyes of an observer 14 wearing the headgear in relation to a reference primary position; and projector means 10 for projecting a target onto a screen spaced from the observer.

13 Claims, 2 Drawing Sheets

METHOD AND APPARATUS FOR OCULAR MOTILITY TESTING

This application is a Continuation-In-Part Application of U.S. application Ser. No. 08/313,051, filed on Sep. 30, 1994 now U.S. Pat. No. 5,550,601.

BACKGROUND OF THE INVENTION

The present invention relates to a method and apparatus for ocular motility testing.

More particularly, the present invention is concerned with the degree of accuracy or error in the direction of gaze of each eye of an observer/patient instructed to look at a target displayed successively at different positions on a screen. Although such testing involves movements of the eyes to redirect the gaze directions towards the different target positions, it should be understood that ocular motility test data consists essentially of static measurements for each specific target position. The present ocular motility testing is not concerned with dynamic measurements during eye movements. However, it is envisaged that ocular motility testing can feature a continuously moving target provided that the speed of movement is not too fast to prevent the obtaining of effective static measurements for different specific target positions.

In this regard, U.S. Pat. No. 5,070,883 to Kasahara discloses a device used for analysing dynamic measurements during eye movement. In this device, a pair of goggles houses a light source, a target and a TV camera for each eye. Whilst this known device can, in certain circumstances, be used to provide ocular motility test results, its use is severely restricted for such applications. This limited applicability arises predominantly because the target distance from the user's eye is fixed (different eye movements result from different distances of the eye from the target) and because the eyes of a user of this known device each see a different target, such that no assessment of how the eyes are working together looking at the same target (binocular vision) can be made. The smallness of the separate screens in the goggles of the Kasahara device moreover restricts the variation, positioning and number of targets that can be displayed, thereby further limiting the scope of tests that may be performed. Moreover, as targets of the Kasahara device are positioned relatively close to the eye, for ocular motility testing initial setting up of the goggles in relation to the visual axis of each eye can be problematic. Furthermore, the closeness of the goggle components to the user's eyes is disadvantageous in that any slight movement of the goggles relative to the user's head will have a large effect in degrading the results. Also, the target is too close to the eye for it to be in focus.

U.S. Pat. No. 5,094,521 to Jolson discloses an apparatus arrangement for evaluating eye alignment. In the Jolson arrangement a target assembly includes a plurality of lamps aligned as targets in predetermined locations on vertical and horizontal arms of an inverted 'T'. A camera positioned at the target measures the position of one eye relative to the other eye. Whilst the arrangement of the Jolson document can again be used to perform ocular motility testing its use in such applications is limited predominantly by the nature of the target. In this connection, the use of lamps on an assembly spaced from the user restricts the colour, positioning, size and variation of the target in relation to the user's eyes. Furthermore, the arrangement requires careful use during measurement since a relative movement between the target assembly and the user's head would have an effect in corrupting the results. Also, in this prior document if an eye is occluded, the camera that would otherwise track that eye's movement cannot see the occluded eye and therefore cannot detect any change in its position or how quickly that change occurs.

The present invention seeks to alleviate the problems associated with the known arrangements discussed above.

SUMMARY OF THE INVENTION

According to a first aspect of the present invention, there is provided apparatus for ocular motility testing comprising:

gaze-direction detection means for determining the visual axis directions of one or both eyes of an observer viewing a target in relation to a reference primary position of one or both eyes detected by the gaze-direction detection means; and projector means for projecting a target to be viewed by the observer onto a screen remote from the observer;

characterised in that the projector means is located at or adjacent the observer's head and coupled thereto so as to prevent relative movement therebetween.

The use of a projector means is particularly advantageous in relation to ocular motility testing. For example, the distance of the projector means (and thus patient) from the screen can be readily varied to thereby analyze the different eye movements that result from such different distances. The angle subtended at the eyes of the observer by a target on the screen will remain the same regardless of how far the screen is from the observer and projector means. Moreover, the use of a projector means allows the target and/or its background to take the form of virtually any shape, size, colour or brightness required. This is useful from a clinical point of view but also from a practical point of view. For example, in order to keep the attention of a difficult child, the target could be projected as a toy or cartoon character. Furthermore, as both eyes can view the same object, assessment of how the eyes work together can be made. The projector means can moreover project the target on any suitable screen. In practice a suitable light coloured wall may be used, thereby foregoing the need for a separate bulky screen.

The projector means, or at least the final projecting element thereof (eg. lens) may be mechanically coupled to the observer's head or signals from movement sensors on the head may be used to revise results that would otherwise be corrupted by relative movement between the projector means and the observer's head.

Preferably, the projector means is in use located close to the observer's eyes. This facilitates the setting up of the reference primary position.

In preferred embodiments, the projector means is mounted onto the observer's head by way of a suitable item of headgear.

Preferably, the projector means is controlled by a computer. In this way the target can either be displayed at different positions or can be moved dynamically along a predetermined path on the screen according to parameters set in a computer program. The target may moreover be moved by an operator by way of the computer.

Conveniently, the projector means is a video projector.

In preferred embodiments, results from the gaze-direction detection means and control instructions for the projector means are fed to and recorded by the computer for analysis.

Preferably, the occluders are LCD computer controlled occluder stops controlled by suitable electrical signals from the computer, to prevent either eye seeing the projected image.

Conveniently, the gaze-direction detection means has associated gaze occluder means operable selectively to occlude the observer's eye relative to the target, without obstructing the gaze-direction detection means. The use of occluder means allows the measurement of a latent squint, that is any misalignment adopted by the occluded eye which develops when that eye cannot see the target but the other eye still can.

According to a second aspect of the present invention there is provided a method of ocular testing comprising the steps of:

(a) detecting the visual axis of at least one eye of an observer instructed to look at a target, (b) computing the position of said visual axis with reference to a primary position, (c) storing the positions of the target and the visual axis, and (d) repeating steps (a–c) for several different target positions thereby to derive ocular motility data;

characterised in that the target is displayed by way of a projector arrangement comprising a projector means located at or adjacent the observer's head.

According to a third aspect of the present invention there is provided apparatus for ocular motility testing comprising, an item of headgear onto which is mounted:

gaze-direction detection means for determining the visual axis directions of one or both eyes of an observer wearing the headgear in relation to a reference primary position; and projector means for projecting a target onto a screen spaced from the observer.

BRIEF DESCRIPTION OF THE DRAWINGS

Other objects, features and advantages of the present invention will be apparent from the written description in the drawings in which.

DESCRIPTION OF THE PREFERRED EMBODIMENTS

Figure 1:
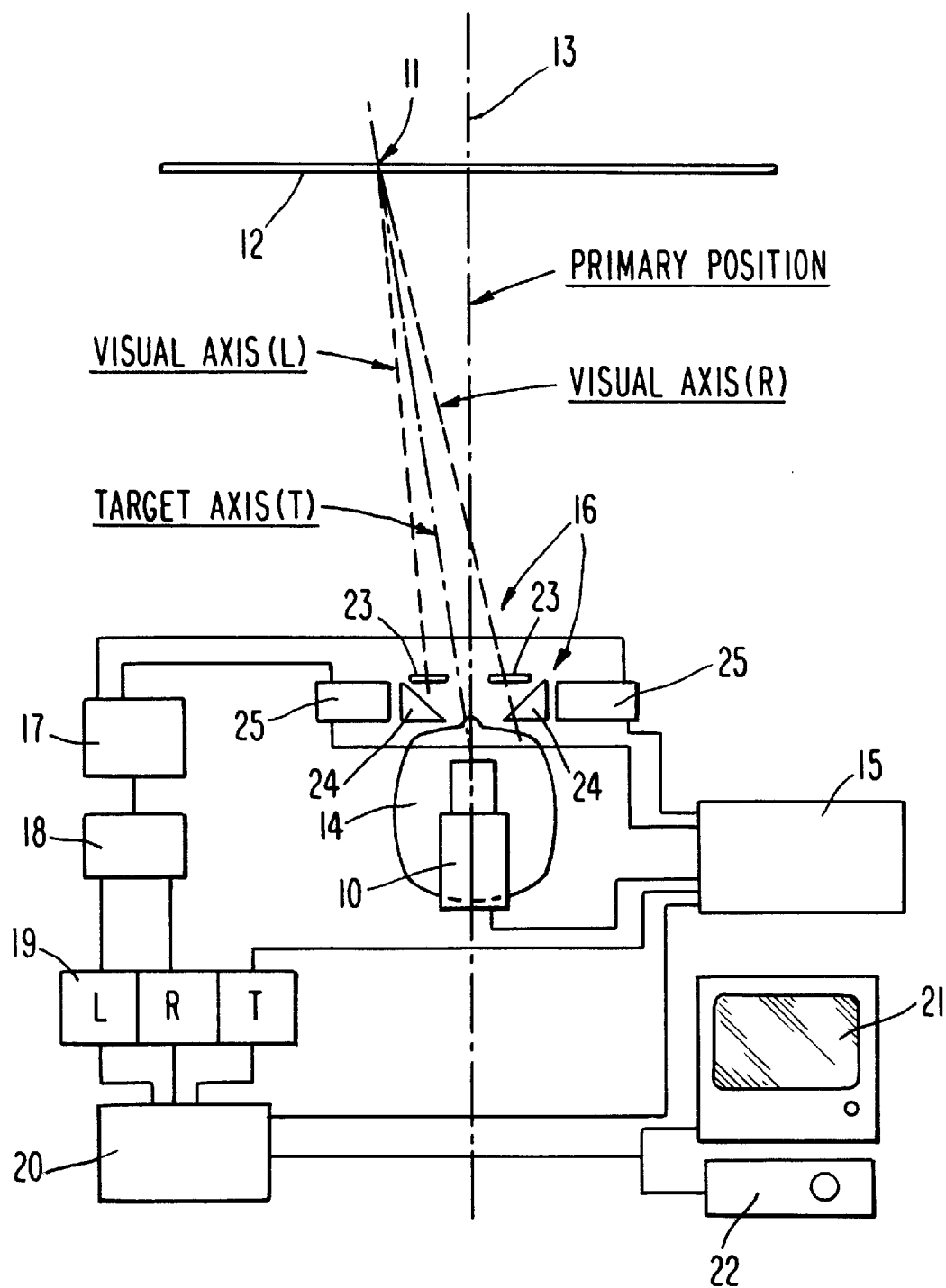
FIG. 1 is a diagrammatic representation in plan view of apparatus for use in ocular motility testing.

In FIG. 1 of the drawings, the apparatus includes a projector 10 adapted to project a target 11, onto screen 12 which is positioned substantially symmetrically with respect to a centre line 13 (primary position—looking straight ahead). An observer/patient 14 is positioned immediately below the projector 10 and on the centre line 13. The screen 12 is preferably flat and may simply comprise a suitable wall surface.

The projector 10 (possibly a video projector unit) is adapted to be capable of projecting the target 11 to any specific position on the screen 12 in response to signals issued by a control console 15 which provides an operator with the choice of moving the target according to a predetermined program and/or selectively to successive different positions.

Figure 2:
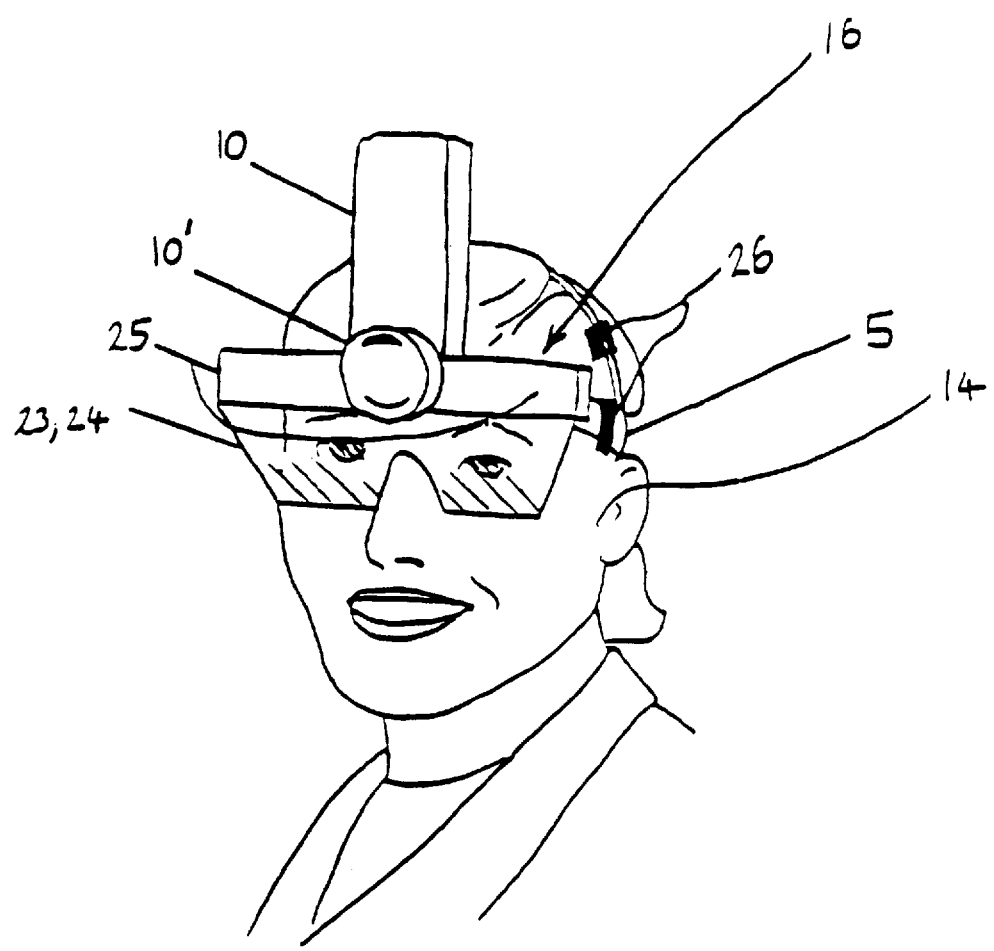
FIG. 2 is a representation of possible headgear to be worn for use with the present invention.

As shown in FIG. 2 the projector 10 and its lens 10' are attached in an integral unit to a head band 5 that fits snugly on the patient's head. Suitable means are provided for moving the projector elements relative to the patient's head and for adjusting the fit of the headband, for example slides 26 or tensioning knobs.

The use of a projector allows that target and background to take the form of virtually any shape, size, colour or brightness. Not only does this increase the flexibility of the system but also from a practical point of view this is advantageous, for example by displaying a toy to keep the attention of a child.

The integral unit further includes detecting means 16 disposed close to the eyes of the observer 14 and on the respective visual axes thereof. The detecting means 16 includes mutually independent left and right gaze-direction detectors 25 (facing inwardly in FIG. 1, but can be in any direction, for example, facing down as in FIG. 2) and occluders 23. Each gaze-direction detector detects eyeball movement and produces signals which can be interpreted to provide data representing the direction of the visual axis vertically and horizontally with reference to the primary position or centre line 13 (see FIG. 1) which would be represented by a point on the projected screen. Polar, co-ordinate or other angular measurements may be used in this respect. Thus, a computing means 17 is adapted to calculate independently the visual axis directions for left and right eyes. Ideally, the central light axis of the projector lens should be the same as the visual axis of each eye but in binocular vision this is technically impossible. The computing means can however be programmed to correct any error of alignment.

In this description and in the appended claims, the term "position" is a reference to any kind or format of data which defines, with reference to the centre line 13 and/or its intersection with the screen 12, the direction of gaze or the direction of the target from the eye.

The occluders 23 associated with the detecting means 16 are operable simply to occlude sight of the target from one or the other eye according to choice of the operator or the program.

It will be noted that whilst an occluded eye cannot see the target, the appropriate detectors 25 can still view the occluded eye or eyes. This is important clinically since a change in gaze direction of an eye that cannot see a target can reveal important information. For example, it may cause a squint to occur which was not present and thus undetected when both eyes can see the target (this is called latent squint). Monitoring the rate of development and the variability of such a squint under occlusion can be important clinically.

The occluders can take the form of LCD computer controlled occluder stops controlled by suitable electrical signals from the computer. Thus in FIG. 2, reference 24 comprises a partially reflecting mirror with a LCD occluder sheet positioned on its anterior surface.

The gaze-direction detectors 25 take the form of cameras provided on the anterior of the headgear. Preferably, infrared sensitive cameras are used which detect infrared light illuminating the eyes and partially reflected by the partially reflecting mirror 24.

Outputs from the computing means 17 are fed to further computing means 18 adapted to calculate, using either polar or co-ordinate values, the positions of the left and right visual axes with reference to the primary position, and these positions are in turn fed to a store means 19. The position of the target 11 is passed directly to the store means 19 from the control console 15. It will be understood that the store means 19 is capable of storing successive different positions of the target 11.

A comparator means 20 is linked with outputs from the store means 19 and is operable in response to the control console 15 to process all of the stored positions to provide correlation information in a form suitable for displaying and/or printing respectively on a visual display unit 21 or printer 22, or for further storage by a further store means 26.

In operation of the apparatus, the observer/patient 14 is simply instructed to look at the target 11 which is moved to successive different positions either step-wise or dynamically according to a program or according to the choice of the operator. The patient's eyes are illuminated by infrared light and partially reflecting mirror 24 is positioned in front of the eyes so that light reflected from the eyes can be detected by the infrared sensitive cameras 25. Without further instruction to the observer 14 and without any other action required from the observer, the eye positions for each eye, or for either eye, are detected and converted to direction data and stored in the store means 19 together with the corresponding data for each of the target positions/directions. If testing is done on a dynamic basis, it will be understood that a sampling time element will be introduced.

Subsequently, under the control of the operator, the stored position data is read out from the store means 19 and processed by means of the comparator 20 for display and/or printing and/or further storage.

In a modification of the system apparatus as described above, the left, right and target position data may effectively be stored directly by means of the visual display unit 21 and/or printer 22, thus by-passing the store means 19 and/or comparator 20. In the foregoing description and in the appended claims, the term "store" and its related terms embraces any medium for keeping a record of multiple data items. In another modification, the screen/projector arrangement is replaced by a video display unit which can be driven in known manner to emulate the screen/projector function. These modifications are within the scope of the appended claims.

I claim:

1. An apparatus for ocular motility testing comprising;

gaze-direction detection means for determining the visual axis directions of one or both eyes of an observer viewing a target in relation to a reference primary position of the one or both eyes detected by the gaze-direction means;

means for projecting a target to be viewed by the observer onto a screen remote from and at an alignment with the observer's head; the projector means being coupled to the observer's head for following movement thereof that may disturb said alignment with the screen.

2. An apparatus according to claim 1, wherein the projector means is in use located close to the observer's eyes, projecting an image in front of the observer.

3. An apparatus according to claim 1, wherein the projector means is mounted onto the observer's head by way of a suitable item of headgear.

4. An apparatus according to claim 1, wherein the projector means is a video projector.

5. An apparatus according to claim 1, wherein the projector means is controlled by a computer.

6. An apparatus according to claim 5, wherein results from the gaze-direction detection means and control instructions for the projector means are fed to the computer for analysis.

7. An apparatus according to claim 1, wherein the gaze-direction detection means include gaze occluder means operable selectively to occlude an observer's eye relative to the target, without obstructing the gaze-direction detection means.

8. An apparatus according to claim 7, wherein the gaze-occluder means are LCD computer controlled occluder stops controlled by suitable electrical signals from the computer.

9. An apparatus for ocular motility testing comprising, an item of headgear onto which is mounted:

gaze-direction detection means for determining the visual axis directions of one or both eyes of an observer wearing the headgear in relation to a reference primary position; and projector means for projecting a target onto a screen spaced from the observer.

10. Apparatus for ocular motility testing comprising;

gaze-direction detection means for determining the visual axis directions of one or both eyes of an observer viewing a target in relation to a reference primary position of the one or both eyes detected by the gaze-direction detection means;

projector means for projecting a target to be viewed by the observer onto a screen remote from and at an alignment with the observer's head; and at least one sensor attached to the observer's head for following movement thereof that may disturb said alignment with the screen, signals from the sensors being usable to revise results produced by the gaze-direction detection means.

11. A method according to claim 10 wherein the projector means is coupled to the observer's head to prevent relative movement therebetween.

12. Apparatus for ocular motility testing comprising;

gaze-direction detection means for determining the visual axis directions of one or both eyes of an observer viewing a target in relation to a reference primary position of the one or both eyes detected by the gaze-direction detection means;

projector means for projecting a target to be viewed by the observer onto a screen remote from and at an alignment with the observer's head.

13. Apparatus according to claim 12, wherein the projector means is coupled to the observer's head to prevent relative movement therebetween.

* * * * *